| United States Patent [19] | [11] Patent Number: 4,931,078 |
| Yamamoto | [45] Date of Patent: Jun. 5, 1990 |

[54] WATER TREATING AGENT

[75] Inventor: Tokuji Yamamoto, Kyoto, Japan

[73] Assignees: Kyoritsu Glass Mfg., Co., Ltd., Osaka; Mitsubishi Rayon Engineering Co., Ltd., Tokyo, both of Japan

[21] Appl. No.: 116,051

[22] Filed: Nov. 2, 1987

[51] Int. Cl.$^5$ ............................................. A01N 25/00
[52] U.S. Cl. ........................................ 71/67; 514/63; 514/64; 514/495; 71/97; 71/DIG. 1
[58] Field of Search .............. 71/DIG. 1, 67; 514/495

[56] References Cited

U.S. PATENT DOCUMENTS 4,500,337  2/1985  Young ..................................... 71/67

OTHER PUBLICATIONS

Tsuchi, W., Chem. Absts. vol. 91 (1979), 43417n.

Tsuzuki, Chem. Absts. vol. 105 (1986) 2230k.

*Primary Examiner*—Glennon H. Hollrah
*Assistant Examiner*—Eric J. Kraus
*Attorney, Agent, or Firm*—Oblon, Spivak, McClelland, Maier & Neustadt

[57] ABSTRACT

This invention relates to a water soluble agent including a water soluble glass containing monovalent silver ions in its glass component. In water or an aqueous solution, the water soluble glass of the invention is capable of releasing the monovalent silver ions as required in an effective amount over a long period, the monovalent silver ions excelling, for example, in eliminating or preventing the occurrence of aquatic bacteria or other aquatic life forms, sterilizing them, preventing the occurrence of algae, and preventing water contamination.

12 Claims, No Drawings

WATER TREATING AGENT

BACKGROUND OF THE INVENTION

1. Field of the Invention

The present invention relates to a water treating agent and, particularly but not exclusively, to a water treating agent suitable for eliminating or preventing the occurrence of aquatic bacteria or other aquatic life forms such as slime or algae which may occur in cooling towers, reservoirs, swimming pools, solar heating systems, or irrigation systems; or for preventing the putrefaction of aqueous suspensions or solutions including organic substances.

2. Description of the Related Art

Bacteria or other aquatic life forms may occur in places in which fresh water is circulated or stored, such as cooling towers, reservoirs, swimming pools, solar heating systems or irrigation systems. The occurrence of such bacteria or aquatic life forms may cause significant maintenance problems with respect to hygiene or cost.

For example, in a cooling tower, if large numbers of bacteria occur, they form a gelatin-like mass, combine with other solid matter to form slime, and cling to the inner wall of tanks or tubes. This may lower the heat conductivity of the portions to which the slime clings, and may lead to local corrosion or pitching. Also, there is a tendency for algae to proliferate in places, such as sprayed pond, charged layers, or vessels, which may be exposed to light. Such algae may hinder the flow of water, and may cause the phenomenon of pitching.

In order to eliminate or prevent the occurrence of such slime or algae, disinfection has heretofore been performed by means of filtration employing a filter, adsorption employing a porous material such as zeolite, or the addition of a chemical such as an organic tin compound. However, none of these conventional methods provide satisfactory effects.

As swimming pools are used more frequently, various problems are encountered such as water contamination due to anomalous growth of colibacilli, or a lowering in purification function due to the occurrence of algae. In order to prevent water contamination in swimming pools, disinfection is carried out employing chlorine. However, as the concentration of chlorine is increased, the eyes or nasal passages of children or young people may be affected or color of swimsuits may be affected.

In addition, while a mixture of water and oil, such as a cutting lubricant, or various other emulsions are stored, organic substances contained in these aqueous solutions may putrefy, with the result that it may become impossible to employ them.

In order to prevent water or aqueous solution from being contaminated by the proliferation of the aforementioned bacteria or microbes, several attempts at employing a cuprous oxide as an effective germicidal component for bacteria or microbes are reported. (See Japanese Patent Laid-open No. 158202/1987 and Japanese Patent Publication No. 49306/1972.) However, although the cupric oxides is stable, a cuprous oxide is relatively unstable. Therefore, when copper is to be used as a component of a germicidal or bactericidal agent, it becomes necessary to cause copper to coexist with a reducing agent. In addition, it is necessary to employ a large amount of a copper compound.

SUMMARY OF THE INVENTION

It is therefore an object of the present invention to provide a water treating agent having a germicidal or bactericidal function which can be adjusted by adding a relatively small number of monovalent silver ions to a water soluble glass used as a base material, the monovalent silver ions having characteristics excellent in a germicidal or bactericidal function.

The aforesaid object and other advantages are achieved by the present invention which provides a water treating agent comprising a water soluble glass containing monovalent silver ions in the glass composition.

The term "water soluble glass" used herein is defined as a water soluble glass whose at least about 10 percent by weight dissolves when it is placed under water over a predetermined period of two or less years.

The water treating agent according to the present invention is capable of, in water or an aqueous solution, releasing monovalent silver ions as required in an effective amount over a long period by controlling the dissolving rate of the water soluble glass used as a base material, the monovalent silver ions excelling, for example, in eliminating or preventing the occurrence of aquatic bacteria or other aquatic life forms, sterilizing them, preventing the occurrence of algae and preventing water contamination.

The water soluble glass may contain a glass component essentially consisting of a network forming oxide containing a combination of $B_2O_3$ and at least one of $SiO_2$ and $P_2O_5$; and a network modifying oxide including at least one selected from the group consisting of $Na_2O$, $K_2O$, $Li_2O$, $CaO$, $MgO$, $BaO$ and $ZnO$, the glass component being combined, as required, with an intermediate oxide such as $Al_2O_3$ or $TiO_2$.

In accordance with the present invention, for example, in the case where a combination of $B_2O_3$ and $SiO_2$ is employed as the network forming oxide, the glass component may preferably include about 5 to about 45 percent $SiO_2$ by weight, about 20 to about 90 percent by weight $B_2O_3$, and about 5 to about 70 percent by weight of a network modifying oxide by weight. Alternatively, the glass component may preferably include about 5 to about 50 percent $SiO_2$ by weight, about 10 to about 40 percent $B_2O_3$ by weight, and about 40 to about 60 percent by weight of a network modifying oxide. In the case where a combination of $B_2O_3$ and $P_2O_5$ is employed as the network forming oxide, the glass component may preferably include about 10 to about 50 percent $B_2O_3$ by weight, about 20 to about 60 percent $P_2O_5$ by weight, and about 25 to about 50 percent by weight of a network modifying oxide.

In accordance with the present invention, the solubility of the water soluble glass may be controlled by adjusting the ratio of the composition of the network forming oxide composed of a combination of $B_2O_3$ and at least one of $SiO_2$ and $P_2O_5$; the network modifying oxide including at least one selected from the group consisting of $Na_2O$, $K_2O$, $Li_2O$, $CaO$, $MgO$, $BaO$ and $ZnO$; and the intermediate oxide such as $Al_2O_3$ or $TiO_2$. In this water soluble glass, silver is stably present in the glass component in the form of monovalent silver ions which are gradually elluted from the surface of the water soluble glass as it dissolves.

In accordance with the present invention, silver ions may be added in the various forms of a silver compound such as silver oxide or silver nitrate. When the water soluble glass containing such silver ions is melted, the silver ions become silver oxide within the water soluble glass. If a water treating agent is constituted by the water soluble glass including monovalent silver ions in the form of silver oxide, it is possible to obtain a persistent water soluble agent from which monovalent silver ions having a germicidal or bactericidal effect is elluted at a fixed rate over a long period. In this case, the persistency of a germicidal effect is greatly improved when compared with a case wherein silver ions alone are added to water. In addition, it is possible to obtain an extremely high germicidal effect per silver-ion concentration which is estimated from the dissolving rate of the water soluble glass. It is considered that this effect is achieved by a synergistic effect of components of the water soluble glass, for example, boric acid acid and silver ions.

Accordingly, in accordance with the present invention, a relatively small number of silver ions may be added to the water soluble glass. More specifically, a relatively small amount of silver ions may be added to the water soluble glass, that is, the water soluble glass may include about 0.1 to 2.5 parts by weight of silver ions (in terms of silver oxide ($Ag_2O$)) with respect to 100 parts by weight of glass component. Even if the amount of silver ions added is further increased, the germicidal effect is no longer improved; rather, the cost may increase.

DESCRIPTION OF THE INVENTION

The present invention will be described in more detail below with reference to the following examples.

A water soluble glass containing monovalent silver ions is obtained by adding about 0.1 to about 2.5 parts by weight of monovalent silver ions (in terms of silver oxide ($Ag_2O$)) per 100 parts by weight of a glass component, and melting the thus-obtained compound. To ensure that the water soluble glass stably incorporates monovalent silver ions, it is preferable to suitably select the ratio of the composition of the network forming oxide to that of the network modifying oxide which constitute the glass component, as well as heat treatment conditions such as the melting point and melting period.

EXAMPLES 1 to 3

In each of Examples 1 to 3, glass materials were uniformly mixed to obtain each of the composition ratios shown in Table 1, and were melted at a temperature of 1100° C. for sixty minutes in a glass-melting furnace. Thereafter, the thus-melted material was quenched to form a water soluble glass containing monovalent silver ions. This water soluble glass was ground by a ball mill and passed through a standard 12-mesh sieve (having 1.68-mm mesh), and through a 32-mesh sieve to obtain selected glass granules, which were washed with alcohol and then dried to obtain a glass water treating agent.

TABLE 1

| Oxide | Example 1 | Example 2 | Example 3 |
|---|---|---|---|
| CaO (mol %) | 30 | — | — |
| ZnO (mol %) | — | 40 | 40 |
| $B_2O_3$ (mol %) | 20 | 30 | 20 |
| $P_2O_5$ (mol %) | 50 | 30 | 40 |
| $Ag_2O$ (wt. %) | 1 | 1 | 1 |

100 cc of distilled water was added to 10.00 grams of each of the thus-produced glass water treating agents, and was heated at 75° C. for 40 minutes then at 80° C. for 260 minutes. Subsequently, the non-dissolved portion of each of the glass water treating agents was collected by a filter separation method, was dried, and the dried agent was weighed to determine how much of the agent had dissolved. Table 2 shows the results. In addition, Table 2 includes the pH value and the weight of monovalent silver ions calculated in terms of the amounts of the agents which dissolved.

TABLE 2

| Item | EXAMPLE 1 | EXAMPLE 2 | EXAMPLE 3 |
|---|---|---|---|
| Amount of Dissolved Glass Water Treating Agent (g) | 0.066 | 0.045 | 0.054 |
| Percentage of Dissolved Glass Water Treating Agent (%) | 0.66 | 0.45 | 0.54 |
| Amount of Monovalent Silver Ions, Calculated in Terms of Dissolved Amount (mg) | 0.66 | 0.45 | 0.54 |
| pH value | 1.8 | 2.0 | 2.0 |
| Color of Solution | Slightly brown | Slightly gray | Slightly grayish white |

As can be seen from Table 2, the water treating agent of this invention is capable of controlling the amount of silver ions elluted by changing the glass composition.

In order to confirm the germicidal effect of these examples, the number of bacteria generated was measured employing an SCD agar medium.

The composition of the SCD agar medium was poly peptone, casein peptone (15%); poly peptone, soy peptone (5%); sodium chloride (5%); agar (15%); and water (60%). The number of bacteria was measured by the following procedure: (1) 1 ml of each of the solutions of Examples 1 to 3 was poured into a laboratory dish. (2) The SCD agar medium was placed on the laboratory dish and was made to gel therein. (3) After cultivation at 35 ±1° C. for 72 hours in a thermostat, the number of bacteria was measured. The results are shown in Table 3, including the result of an experiment employing distilled water and the tap water of Osaka, Japan.

TABLE 3

| Number of Experiments | Example 1 | Example 2 | Example 3 | Distilled Water | Tap Water |
|---|---|---|---|---|---|
| 1 | 0 | 23 | 0 | *1 | *1 |
| 2 | 0 | 7 | 0 | | |
| 3 | 0 | 0 | 0 | | |
| Average | 0 | 10 | 0 | | |

*1 Since too many bacteria proliferated, it is impossible to measure the number. It is estimated that the number of bacteria exceeded ten thousand.

In the case of Example 2 alone, an extremely small number of bacteria was observed. However, it will be understood from Table 3 that the glass water treating agent of this invention provides a superior effect on sterilization.

EXAMPLE 4

Example 4 illustrates a sterilization effect and an anti-algae effect obtained in a cooling tower.

0.5 percent by weight of monovalent silver ions (in terms of $Ag_2O$) was added to an oxide including 10.0 mol % $Na_2O$, 50.0 mol % $B_2O_3$, and 40.0 mol % $SiO_2$ to prepare a glass water treating agent. 7 kg of the thus-prepared glass water treating agent mass having a diameter of 5 to 10 mm was placed in a cooling tower which circulates 10 tons of water, and changes in the water quality with time were observed. The results are shown in Table 4 -1.

TABLE 4-1

| Item | Before Use | Day 21st | 58th |
|---|---|---|---|
| pH Value (20° C.) | 7.2 | 7.3 | 7.4 |
| Chromaticity (degree) | 24 | 16 | 5 |
| Turbidness (degree) | 20 | 10 | 1 or less |
| Calcium Hardness (mg/l) | 12 | 28 | 43 |
| Magnesium Hardness (mg/l) | 8.0 | 14 | 12 |
| Concentration of Free Silicic Acid (mg/l) | 8.7 | 25 | 22 |
| Slime | Adhered to inner walls at a large amount | Substantially removed | Not observed |
| Algae | Small number present | Not observed | Not observed |
| Floating Material | Light brown turbidness | Extremely small number of white grains | Turbidness was not observed |

As can be seen from the results shown in Table 4-1, when the glass water treating agent having the composition of Example 4 was applied to a cooling tower, the slime which adhered to the inner walls of the cooling tower was removed, no algae were observed over a long period, and the levels of chromaticity and turbidness were lowered, thereby proving that water contamination was reduced. Accordingly, it will be appreciated that the glass water treating agent provides a germicidal effect, an anti-algae effect, and an effect of reducing water contamination.

COMPARATIVE EXAMPLE 1

Instead of 7 kg of a glass water treating agent mass, 140 g of silver oxide was added under the same conditions as those of Example 4. Over three days after the addition, the amount of slime continued to decrease and no algae were observed. Thereafter, however, slime gradually began to adhere to the inner walls of the cooling tower. On the 21st day, no great difference was to be observed between the states subsisting before and after addition in terms of chromaticity, turbidness, the amount of slime, the number of algae, and the state of floating material.

The comparison of the Example 4 and Comparative example 1 demonstrates that, even if silver oxide alone is employed in an amount equivalent to several times the amount of silver ions contained in the water treating agent of the present invention, no long-term effect is observed. In contrast, the water treating agent of the present invention exhibits a satisfactory effect (e.g., as in Example 4) in spite of the fact that the amount of silver ions elluted from the water soluble glass is very small relative to the total amount of silver contained therein as compared with the dissolving rate of the water soluble glass.

It is therefore considered that a synergistic effect arising from the presence of both silver ions and water soluble glass takes place during use of the water treating agent of the invention as well as the effect provided by progressive release of silver ions.

COMPARATIVE EXAMPLE 2

A glass water treating agent containing 0.08 percent by weight of monovalent silver ions (in terms of $Ag_2O$) was employed under the same conditions as those of Example 4.

The results are shown in Table 4 - 2.

TABLE 4-2

| Item | Before Use | Day 21st | 58th |
|---|---|---|---|
| pH Value (20° C.) | 7.2 | 7.3 | 7.4 |
| Chromaticity (degree) | 24 | 22 | 23 |
| Turbidness (degree) | 20 | 20 | 19 |
| Calcium Hardness (mg/l) | 12 | 28 | 43 |
| Magnesium Hardness (mg/l) | 8.0 | 14 | 12 |
| Concentration of Free Silicic Acid (mg/l) | 8.7 | 25 | 22 |
| Slime | Adhered to inner walls at a large amount | Very slightly removed | Slightly removed |
| Algae | Small number present | Small number present | Small number present |
| Floating Material | Light brown turbidness | Light brown turbidness | Light brown turbidness |

EXAMPLE 5 and COMPARATIVE EXAMPLE 3

Example 5 illustrates fungicidal effect on mold growing on cheese.

0.5 percent by weight of monovalent silver ions (in terms of $Ag_2O$) were added to an oxide including 40.0 mol % $Na_2O$, 30.0 mol % $B_2O_3$, and 30.0 mol % $SiO_2$ to prepare a glass water treating agent. A rectangular piece of cheese of about 30 grams was cut into two equal parts. The parts were separately placed on two laboratory dishes, and 60 cc of tap water was poured into each dish. Subsequently, 1.3 grams of a glass water treating agent having the above-described composition was placed on one of the laboratory dishes to prepare a sample of Example 5, while nothing was added to the other for a sample of Comparative Example 3. The two dishes were placed at room temperature (15° to 20° C.), and changes with time were observed. Table 5 shows the results of this observation. It was noted that the weight of the glass water treating agent was not reduced by any measurable level after the experiments.

TABLE 5

| | Example 5 Water Treating Agent was added. | | Comparative Example 3 Water Treating Agent was not added. | |
|---|---|---|---|---|
| Day | Cheese | Water | Cheese | Water |
| 2nd | No change | No change | Small amount of mold appeared | No change |
| 3rd | No change | No change | Colored brown mold increased | Slightly turbid (white) |
| 5th | No change | Slightly turbid (white) | Colored blackish brown, Mold further increased | Colored light, Mold grew |
| 12th | No change | *2 | Blackish brown | Mold prolifi- |

TABLE 5-continued

| | Example 5 Water Treating Agent was added. | | Comparative Example 3 Water Treating Agent was not added. | |
|---|---|---|---|---|
| Day | Cheese | Water | Cheese | Water |
| | | | mold further increased, shed offensive odor | erated, yellowish-brown turbid |

*2 The degree of white turbidity increased slightly, but the degree of transparency did not change.

As can be seen from the results shown in Table 5, the glass water treating agent having the composition of Example 5 has a fungicidal effect which prevents the growth of bacteria.

COMPARATIVE EXAMPLE 4 AND EXAMPLES 6, 7

Comparative example 4 and Examples 6, 7 illustrate an anti-contamination effect which prevents the growth of sea algae.

The glass water treating agent employed in each of Comparative example 4 and Examples 6, 7 included a glass component having an oxide composition such as that shown in Table 6. The rate of dissolving of a mass of the glass was 0.3 to 0.4% per day.

TABLE 6

| Oxide | Comparative Example 4 | Example 6 | Example 7 |
|---|---|---|---|
| $Na_2O$ (wt. %) | 6.2 | 6.2 | 6.2 |
| $Al_2O_3$ (wt. %) | 0.2 | 0.2 | 0.2 |
| $B_2O_3$ (wt. %) | 69.6 | 69.4 | 69.2 |
| $SiO_2$ (wt. %) | 24.0 | 23.9 | 23.8 |
| $Ag_2O$ (wt. %) | — | 0.3 | 0.6 |

Three stones having a diameter of about 1.5 cm to which sea lettuces had adhered were collected at the bottom of the sea, and they were separately immersed in 20<i>l</i> of sea water contained in containers. Then, about 10 g of a mass of the glass of each of Comparative Example 4 and Examples 6, 7 was placed in each of the three polyvinyl containers. Subsequently, variations with time were observed. Table 7 shows changes in algae of the stones.

TABLE 7

| Day | Comparative Example 4 | Example 6 | Example 7 |
|---|---|---|---|
| 2nd | No change | No change | Turned slightly black |
| 4th | No change | Algae turned black | Turned black and peeled |
| 6th | No change | Partially peeled | — |

It will be understood from the result of Table 7 that the anti-contamination effect was obtained only when the glass water treating agent contained monovalent silver ions. In addition, it was found that, when a rapid anti-contamination effect for sea water was needed, about 0.01 or more ppm of monovalent silver ions were preferably added to sea water.

The results of the above Examples 1, 6 and 7 were obtained from experiments with relatively large sea lettuces living in sea water. However, it will be appreciated that Examples 6 and 7 further produce an effect on relatively small algae which grow in a fresh-water swimming pool.

As previously described, each of the water treating agents of Examples 1 to 5 and Comparative Example 1 included grains which passed through a 12-mesh standard sieve but were retained by a 32-mesh standard sieve. 10 g of each of the water treating agents were placed in 1 l of distilled water at room temperature for 60 days. Subsequently, the amount of each of the agents dissolved was measured on the basis of the amount of the residual matter obtained by filtration. In consequence, it was found that, in any of the above Examples, 15 or more percent by weight of the water treating agent was dissolved.

What is claimed is:

1. A microbicide water treating agent, comprising a water soluble glass containing monovalent silver ions in the form of silver oxide, wherein said water soluble glass comprises a glass component consisting essentially of a network forming oxide containing a combination of $B_2O_3$ and at least one member selected from the group consisting of $SiO_2$ and $P_2O_5$; and a network modifying oxide composed of at least one member selected from the group consisting of $Na_2O$, $K_2O$, $CaO$, $MgO$, $BaO$, $ZnO$, and $Li_2O$.

2. A microbicide water treating agent according to claim 1, wherein said monovalent silver ions are contained at about 0.1 to about 2.5 parts by weight in terms of silver oxide per 100 parts by weight of said glass component.

3. The microbicide water treating agent of claim 1, wherein said glass component consists essentially of about 5 to about 45% by weight $SiO_2$, about 20 to about 90% by weight $B_2O_3$, and about 5 to about 70% by weight of said network modifying oxide.

4. The microbicide water treating agent of claim 1, wherein said glass component consists essentially of about 5 to about 50% by weight $SiO_2$, about 10 to about 40% by weight $B_2O_3$, and about 40 to about 60% by weight of said network modifying oxide.

5. The microbicide water treating agent of claim 1, wherein said glass component consists essentially of about 10 to about 50% by weight $B_2O_3$, about 20 to about 60% by weight $P_2O_5$, and about 25 to about 50% by weight of said network modifying oxide.

6. A method for treating water, comprising contacting water with a microbicide water treating agent, comprising a water soluble glass containing monovalent silver ions in the form of silver oxide, wherein said water soluble glass comprises a glass component consisting essentially of a network forming oxide containing a combination of $B_2O_3$ and at least one member selected from the group consisting of $SiO_2$ and $P_2O_5$; and a network modifying oxide composed of at least one member selected from the group consisting of $Na_2O$, $K_2O$, $CaO$, $MgO$, $BaO$, $ZnO$, and $Li_2O$.

7. The method of claim 6, wherein said microbicide water treating agent, said monovalent silver ions are contained at about 0.1 to about 2.5 parts by weight in terms of silver oxide per 100 parts by weight of said glass component.

8. The method of claim 6, wherein in said microbicide water treating agent, said glass component consists essentially of about 5 to about 45% by weight $SiO_2$, about 20 to about 90% by weight $B_2O_3$, and about 5 to about 70% by weight of said network modifying oxide.

9. The method of claim 6, wherein in said microbicide water treating agent, said glass component consists essentially of about 5 to about 50% by weight $SiO_2$, about 10 to about 40% by weight $B_2O_3$, and about 40 to about 60% by weight of said network modifying oxide.

10. The method of claim 6, wherein in said microbicide water treating agent, said glass component consists essentially of about 10 to about 50% by weight $B_2O_3$, about 20 to about 60% by weight $P_2O_5$, and about 25 to about 50% by weight of said network modifying oxide.

11. A microbicide water treating agent produced by a process comprising the steps of:

(i) adding a silver compound selected from the group consisting of silver oxide and silver nitrate to a mixture of water-soluble glass component materials, to obtain a silver-containing mixture;

(ii) melting said silver-containing mixture to obtain a molten glass; and (iii) cooling said molten glass.

12. A microbicide water treating agent according to claim 11, wherein said water soluble glass comprises a glass component essentially consisting of a network forming oxide containing a combination of $B_2O_3$ and at least one of $SiO_2$ and $P_2O_5$; and a network modifying oxide composed of at least one selected from the group consisting of $Na_2O$, $K_2O$, $CaO$, $MgO$, $BaO$, $ZnO$, and $Li_2O$.

* * * * *